United States Patent [19]  
Alig et al.

[11] 4,137,269  
[45] Jan. 30, 1979

[54] D-HOMOSTEROIDS

[75] Inventors: Leo Alig, Liestal; Andor Fürst, Basel; Marcel Müller, Frenkendorf, all of Switzerland; Ulrich Kerb; Klaus Kieslich; Rudolf Wiechert, all of Berlin, Germany

[73] Assignee: Hoffmann-La Roche Inc., Nutley, N.J.

[21] Appl. No.: 731,238

[22] Filed: Oct. 12, 1976

[30] Foreign Application Priority Data

Oct. 22, 1975 [CH] Switzerland ..................... 13665/75
Jul. 30, 1976 [CH] Switzerland ..................... 9762/76

[51] Int. Cl.² .......................................... C07J 63/00
[52] U.S. Cl. .............................. 260/586 E; 260/408; 260/410; 260/457; 260/946; 424/214; 424/303; 424/305; 424/308; 424/311; 424/312; 424/313; 424/331; 560/1; 560/105; 560/107; 560/122; 560/180; 560/182; 560/194; 560/257

[58] Field of Search .......... 260/586 E, 488 B, 485 G, 260/485 F, 410, 408, 476 C, 457, 946, 468 R, 484 B, 484 R; 560/257

[56] References Cited

U.S. PATENT DOCUMENTS 3,939,193  2/1976  Alig et al. ................... 260/488 B
4,025,563  5/1977  Nickolson et al. ........... 260/488 B
4,026,921  5/1977  Furst ........................... 260/488 B Primary Examiner—Vivian Garner  
Attorney, Agent, or Firm—Jon S. Saxe; George M. Gould; Raymond R. Wittekind

[57] ABSTRACT

The present disclosure relates to steroids. More particularly, the disclosure is concerned with D-homosteroids, a process for the manufacture thereof and pharmaceutical preparations containing same. The subject D-homosteroids have high endocrinal activity and are particularly active as anti-inflammatory agents.

2 Claims, No Drawings

D-HOMOSTEROIDS

BACKGROUND OF THE INVENTION

D-homo cortisone is described in U.S. Pat. No. 2,860,158. D-homo-prednisolone is described in U.S. patent application Ser. No. 345,149, filed Mar. 26, 1973, Alig et al, now abandoned.

DESCRIPTION OF THE INVENTION

The D-homosteroids provided by the present invention have the following general formula

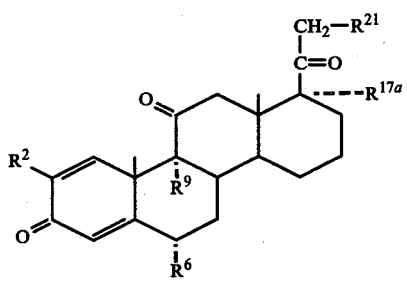

wherein $R^2$ represents a hydrogen or chlorine atom; $R^6$ represents a hydrogen, fluorine or chlorine atom or a methyl group; $R^9$ represents a hydrogen, fluorine, chlorine or bromine atom; $R^{17a}$ represents a hydrogen atom or a hydroxy or acyloxy group and $R^{21}$ represents a hydrogen or halogen atom, a hydroxyl or acyloxy group, a sulphate or phosphate radical or the radical of a dicarboxylic or tricarboxylic acid, which may be in the form of a water-soluble salt.

As used in this specification, the term "halogen" means fluorine, chlorine, bromine or iodine. An acyloxy group can be derived from a saturated or unsaturated aliphatic monocarboxylic acid, a cycloaliphatic, araliphatic or aromatic monocarboxylic acid which preferably contains up to 15 carbon atoms. Examples of such acids are formic acid, acetic acid, pivalic acid, propionic acid, butyric acid, caproic acid, oenanthic acid, undecylenic acid, oleic acid, cyclopentylpropionic acid, cyclohexylpropionic acid, phenylacetic acid and benzoic acid. Especially preferred acyloxy groups are alkanoyloxy groups containing from 1 to 7 carbon atoms. A radical of a dicarboxylic or tricarboxylic acid can be derived, for example, from oxalic acid, malonic acid, succinic acid, fumaric acid, malic acid, tartaric acid or citric acid, preferably from succinic acid. Examples of water-soluble salts of these acid radicals are primarily the alkali metal salts (e.g. the sodium or potassium salts) and the ammonium salts.

A preferred class of D-homosteroids of formula I comprises those in which $R^6$ represents a hydrogen atom or a methyl group, $R^9$ represents a hydrogen or fluorine atom, $R^{17a}$ represents a hydroxy group or an alkanoyloxy group containing from 1 to 7 carbon atoms and $R^{21}$ represents a halogen atom, a hydroxy group or an alkanoyloxy group containing from 1 to 6 carbon atoms.

Examples of D-homosteroids of formula I are:
6α-Chloro-17a,21-dihydroxy-D-homopregna-1,4-diene-3,11,20-trione,
6α-fluoro-17a,21-dihydroxy-D-homopregna-1,4-diene-3,11,20-trione,
17a,21-dihydroxy-6α-methyl-D-homopregna-1,4-diene-3,11,20-trione,
6α-chloro-9-fluoro-17a,21-dihydroxy-D-homopregna-1,4-diene-3,11,20-trione,
6α,9-difluoro-17a,21-dihydroxy-D-homopregna-1,4-diene-3,11,20-trione,
9-fluoro-17a,21-dihydroxy-6α-methyl-D-homopregna-1,4-diene-3,11,20-trione,
9-chloro-17a,21-dihydroxy-D-homopregna-1,4-diene-3,11,20-trione,
9-bromo-17a,21-dihydroxy-D-homopregna-1,4-diene-3,11,20-trione,
9-chloro-17a,21-dihydroxy-6α-methyl-D-homopregna-1,4-diene-3,11,20-trione,
9-bromo-17a,21-dihydroxy-6α-methyl-D-homopregna-1,4-diene-3,11,20-trione,
9-chloro-6α-fluoro-17a,21-dihydroxy-D-homopregna-1,4-diene-3,11,20-trione,
9-bromo-6α-fluoro-17a,21-dihydroxy-D-homopregna-1,4-diene-3,11,20-trione,
21-hydroxy-D-homopregna-1,4-diene-3,11,20-trione,
9-fluoro-21-hydroxy-D-homopregna-1,4-diene-3,11,20-trione,
6α-fluoro-21-hydroxy-D-homopregna-1,4-diene-3,11,20-trione,
21-hydroxy-6α-methyl-D-homopregna-1,4-diene-3,11,20-trione,
6α,9-difluoro-21-hydroxy-D-homopregna-1,4-diene-3,11,20-trione,
9-fluoro-21-hydroxy-6α-methyl-D-homopregna-1,4-diene-3,11,20-trione,
2-chloro-17a,21-dihydroxy-D-homopregna-1,4-diene-3,11,20-trione,
2-chloro-6α-fluoro-17a,21-dihydroxy-D-homopregna-1,4-diene-3,11,20-trione,
2-chloro-9-fluoro-17a,21-dihydroxy-D-homopregna-1,4-diene-3,11,20-trione,
2-chloro-17a,21-dihydroxy-6α-methyl-D-homopregna-1,4-diene-3,11,20-trione,
2-chloro-6α,9-difluoro-17a,21-dihydroxy-D-homopregna-1,4-diene-3,11,20-trione,
2-chloro-9-fluoro-17a,21-dihydroxy-6α-methyl-D-homopregna-1,4-diene-3,11,20-trione,
2-chloro-21-hydroxy-D-homopregna-1,4-diene-3,11,20-trione,
2-chloro-6α-fluoro-21-hydroxy-D-homopregna-1,4-diene-3,11,20-trione,
2-chloro-9-fluoro-21-hydroxy-D-homopregna-1,4-diene-3,11,20-trione,
2-chloro-21-hydroxy-6α-methyl-D-homopregna-1,4-diene-3,11,20-trione,
2-chloro-6α,9-difluoro-21-hydroxy-D-homopregna-1,4-diene-3,11,20-trione,
2-chloro-9-fluoro-21-hydroxy-6α-methyl-D-homopregna-1,4-diene-3,11,20-trione, and 17a- esters and/or 21-esters of the aforementioned D-homosteroids with acetic acid, propionic acid, butyric acid, valeric acid, succinic acid, phosphoric acid and sulphuric acid or sodium, potassium and ammonium salts thereof:
2,21-Dichloro-17a-hydroxy-D-homopregna-1,4-diene-3,11,20-trione,
21-chloro-17a-hydroxy-D-homopregna-1,4-diene-3,11,20-trione,
21-chloro-6α-fluoro-17a-hydroxy-D-homopregna-1,4-diene-3,11,20-trione,
21-chloro-17a-hydroxy-6α-methyl-D-homopregna-1,4-diene-3,11,20-trione,
21-chloro-9-fluoro-17a-hydroxy-2-homopregna-1,4-diene-3,11,20-trione, 2,21-dichloro-6α,9-difluoro-17a-hydroxy-D-homopregna-1,4-diene-3,11,20-trione,
and 17a-propionates, acetates, butyrates and valerates of the aforementioned D-homosteroids:
17a,21-Diacetoxy-D-homopregna-1,4-diene-3,11,20-trione,
17a,21-dipropionyloxy-D-homopregna-1,4-diene-3,11,20-trione,
17a,21-dibutyryloxy-D-homopregna-1,4-diene-3,11,20-trione,
17a,21-divaleryloxy-D-homopregna-1,4-diene-3,11,20-trione,
D-homoprednisone 21-sulphate,
D-homoprednisone 21-phosphate,
sodium D-homoprednisone 21-sulphate,
potassium D-homoprednisone 21-phosphate,
17a,21-diacetoxy-9-fluoro-D-homopregna-1,4-diene-3,11,20-trione,
17a,21-dibutyryloxy-9-fluoro-D-homopregna-1,4-diene-3,11,20-trione,
9-fluoro-17a,21-divaleryloxy-D-homopregna-1,4-diene-3,11,20-trione,
9-fluoro-D-homoprednisone 21-sulphate,
9-fluoro-D-homoprednisone 21-phosphate,
9-fluoro-D-homoprednisone 21-hemisuccinate,
ammonium 9-fluoro-D-homoprednisone 21-sulphate,
potassium 9-fluoro-D-homoprednisone 21-phosphate,
sodium 9-fluoro-D-homoprednisone 21-hemisuccinate.

According to the process provided by the present invention, the D-homosteroids of formula I are manufactured by (a) oxidising the 11-hydroxyl group in a D-homosteroid of the general formula

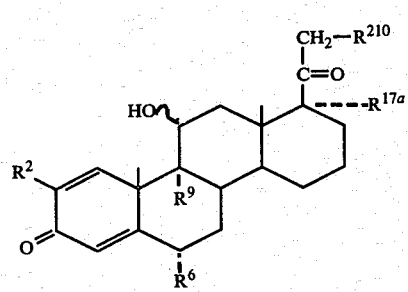
(II)

, wherein $R^{210}$ represents a hydrogen or halogen atom or an acyloxy group and $R^2$, $R^6$, $R^9$ and $R^{17a}$ have the significance given earlier, or (b) chlorinating a D-homosteroid of the general formula

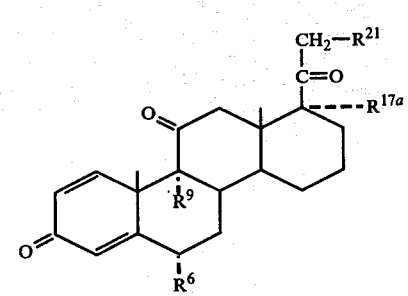
(III)

, wherein $R^6$, $R^9$, $R^{17a}$ and $R^{21}$ have the significance given earlier, in the 2-position, or (c) dehydrogenating a D-homosteroid of the general formula

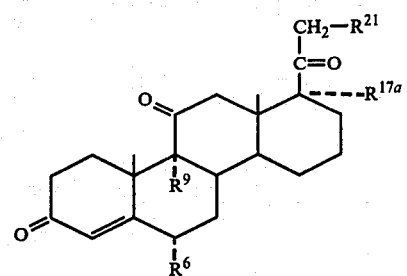
(IV)

, wherein $R^6$, $R^9$, $R^{17a}$ and $R^{21}$ have the significance given earlier, in the 1,2-position, or (d) halogenating a D-homosteroid of the general formula

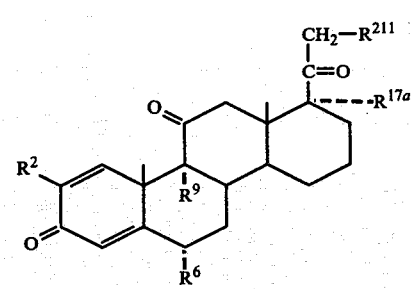
(V)

, wherein $R^2$, $R^6$, $R^9$ and $R^{17a}$ have the significance given earlier and $R^{211}$ represents a hydrogen atom or a hydroxy group, in the 21-position, or (e) treating a D-homosteroid of the general formula

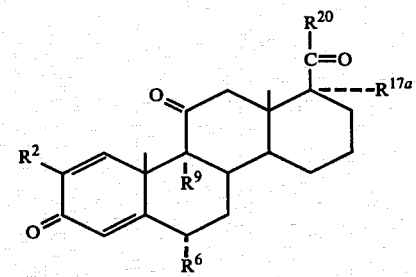
(VI)

, wherein $R^2$, $R^6$, $R^9$ and $R^{17a}$ have the significance given earlier and $R^{20}$ represents a hydroxymethyl, halomethyl or diiodomethyl group, with an acylating agent, or (f) converting the group denoted by $R^{20}$ in a D-homosteroid of formula VI into a group of the formula —$CH_2$—R in which R represents a sulphate or phosphate radical, or (g) saponifying an acyloxy group in a D-homosteroid of formula I in which at least one of $R^{17a}$ and $R^{21}$ represents an acyloxy group, or (h) oxidising the 17a(20)-double bond of a D-homosteroid of the general formula

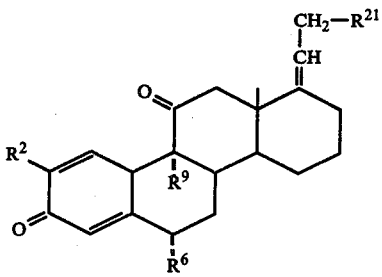

(VII)

, wherein $R^2$, $R^6$, $R^9$ and $R^{21}$ have the significance given earlier, to the hydroxyketone grouping; said embodiments (a) to (h) being carried out in a manner known per se.

The oxidation of the 11-hydroxyl group in a D-homosteroid of formula II in accordance with embodiment (a) of the process can be carried out, for example, using chromium trioxide/glacial acetic acid or chromium trioxide/pyridine or Jones' Reagent.

The chlorination of a D-homosteroid of formula III in the 2-position in accordance with embodiment (b) of the process can be carried out, for example, by treatment with chlorine, in particular a solution of a chlorine in glacial acetic acid or propionic acid, and subsequent dehydrochlorination (e.g. with an organic base, such as pyridine, collidine or dimethylaniline).

The 1,2-dehydrogenation of a D-homosteroid of formula IV in accordance with embodiment (c) of the process can be carried out, for example, in a microbiological manner or using a dehydrogenation agent such as iodine pentoxide, periodic acid, selenium dioxide, 2,3-dichloro-5,6-dicyanobenzoquinone, chloranil or lead tetraacetate. Suitable microorganisms which may be used for the 1,2-dehydrogenation are, for example, Schizomycetes, in particular those of the genera Arthrobacter (e.g. A. simplex ATCC 6946), Bacillus (e.g. B. lentus ATCC 13805 and B. sphaericus ATCC 7055), Pseudomonas (e.g. P. aeruginosa IFO 3505), Flavobacterium (e.g. F. flavescens IFO 3058), Lactobacillus (e.g. L. brevis IFO 3345) and Nocardia (e.g. N. opaca ATCC 4276).

The halogenation of a D-homosteroid of formula V in the 21-position in accordance with embodiment (d) of the process can be carried out by reacting such a compound, in which $R^{211}$ represents a hydrogen atom with elemental chlorine, bromine or iodine in acid solution, if desired with the protection of a 3-keto-$\Delta^4$-system or a 3-keto-$\Delta^{1,4}$-system (e.g. in the form of a 3-enaminium salt such as a 3-pyrrolidinium-enamine). However, the halogenation can also be carried out using a D-homosteroid of formula V in which $R^{211}$ represents a hydroxy group, suitably via the mesylate or tosylate, by reaction with an alkali metal halide (e.g. sodium fluoride, sodium chloride or lithium chloride) or with carbon tetrachloride in triphenylphosphine/dimethylformamide.

The acylation of free hydroxyl groups in the 17a- and/or 21-position of a D-homosteroid of formula VI in accordance with embodiment (e) of the process can be carried out by treatment with an acylating agent such as an acid chloride or anhydride (e.g. acetyl chloride or succinic anhydride), preferably in the presence of an acid-binding agent such as pyridine. The acylation of a 17a-hydroxyl group is conveniently carried out in the presence of an acid catalyst such as p-toluenesulphonic acid, perchloric acid or hydrochloric acid.

The selective introduction of an acyl group in the 21-position can be carried out by replacing a halogen atom present in the 21-position of a D-homosteroid of formula VI by an acyloxy group; for example, by warming a D-homosteroid of formula VI in which $R^{20}$ represents a halomethyl group with an appropriate alkali metal acylate or ammonium acylate in the presence of the acid corresponding to the acylate (e.g. potassium acetate in glacial acetic acid).

In a special aspect, a methyl group present in the 20-position can initially be converted into a diiodomethyl group in a manner known per se by reaction with iodine and the reaction product can be treated with an appropriate acylating agent (e.g. glacial acetic acid in the presence of a base such as diethylamine).

The introduction of a phosphate or sulphate radical into the 21-position of a D-homosteroid of formula VI in accordance with embodiment (f) of the process can be carried out by reacting with a phosphate or sulphate (e.g. an alkali metal hydrogen phosphate or sulphate or with sulphur trioxide in pyridine); the reaction being carried out in an analogous manner to that described in connection with embodiment (e) hereinbefore.

The saponification of an acyloxy group in a D-homosteroid of formula I in accordance with embodiment (g) of the process can be carried out, for example, using aqueous-methanolic potassium carbonate solution.

The oxidation of the 17a(20)-double bond of a D-homosteroid of formula VII in accordance with embodiment (h) of the process can be carried out, for example, using an oxidising agent such as a tertiary amine N-oxide peroxide in tert.butanol/pyridine in the presence of catalytic amounts of osmium tetroxide. Examples of tertiary amine N-oxide peroxides are N-methylmorpholine N-oxide peroxide and triethylamine oxide peroxide. Alternatively, the oxidation can be carried out using an oxidising agent such as osmium tertroxide or permanganate to give the 17a,20-glycol which can be further oxidised to the hydroxyketone using an oxidising agent such as chromic acid.

Unless they are not known or described hereinafter, the starting materials used in the present process can be prepared according to known methods or methods described in the Examples which follow.

Starting materials of formulae V, VI and VII can be prepared from corresponding known compounds containing a 11-hydroxy group by oxidation in a manner analogous to that described in connection with embodiment (a) of the process. Starting materials of formula II containing a 11α-hydroxy group can be prepared from corresponding 11-unsubstituted compounds using microorganisms which hydroxylate steroids in the 11α-position.

The D-homosteroids of formula I possess a high endocrinal, in particular anti-inflammatory, activity. This high activity appears to be surprising, since it has been disclosed (J. Am. Chem. Soc. 80, 3398) that D-homocortisone acetate only has one-third to one-half of the hormone activity of cortisone acetate.

The D-homosteroids of formula I can be used as medicaments: for example, in the form of pharmaceutical preparations which contain them in association with a compatible pharmaceutical carrier material. This carrier material may be an organic or inorganic inert carrier material which is suitable for enteral, percutaneous or parenteral administration such as, for example, water, gelatine, gum arabic, lactose, starch, magnesium stearate, talc, vegetable oils, polyalkylene glycols, petroleum jelly and the like. The pharmaceutical preparations can be made up in a solid form (e.g. as tablets, dragées, suppositories or capsules), in a semi-solid form (e.g. as ointments) or in a liquid form (e.g. as solutions, suspensions or emulsions). The pharmaceutical preparations may be sterilised and/or may contain adjuvants such as preservatives, stabilisers, wetting agents, emulsifiers, salts for altering the osmotic pressure or buffers. They can also contain other therapeutically valuable substances.

Pharmaceutical preparations for topical administration may contain, for example, from about 0.01% to 1% of a D-homosteroid of formula I. Pharmaceutical preparations for systemic administration may contain, for example, from about 0.1 mg to 10 mg per dosage unit.

The pharmaceutical preparations can be produced in a manner known per se by mixing a D-homosteroid of formula I with non-toxic solid and/or liquid carrier materials which are customary in pharmaceutical preparations and which are suitable for therapeutic administration (e.g. the carrier materials mentioned earlier) and, where necessary, transforming the mixture into the desired pharmaceutical dosage form.

The following Examples illustrate the process provided by the present invention:

EXAMPLE 1

0.9 ml of Jones' Reagent was added to 1.2 g of 21-butyryloxy-11β,17a-dihydroxy-D-homopregna-1,4-diene-3,20-dione in 110 ml of acetone at 5° C. and the mixture was stirred for 10 minutes. After the addition of 1 ml of methanol, the mixture was concentrated in vacuo. The residue was taken up in methylene chloride and ice-water. The aqueous phase was extracted three times with methylene chloride and the methylene chloride solutions were washed with dilute sodium chloride solution, dried and evaporated in vacuo. After chromatography on silica gel with methylene chloride/acetone and crystallisation of the pure fractions from methanol, there were obtained 730 mg of 21-butyryloxy-17a-hydroxy-D-homopregna-1,4-diene-3,11,20-trione; melting point 120°–122° C.; $[\alpha]_D = +140°$ (c = 0.109% in dioxan); UV: $\epsilon_{239} = 13,500$.

In an analogous manner, from 21-acetoxy-11β,17α-dihydroxy-D-homopregna-1,4-diene-3,20-dione there was obtained 21-acetoxy-17a-hydroxy-D-homopregna-1,4-diene-3,11,20-trione; melting point 230°–231° C. (from acetone/hexane); $[\alpha]_D = +162°$ (c = 0.103% in dioxan); UV: $\epsilon_{239} = 13,900$;

from 21-acetoxy-11α,17a-dihydroxy-6α-methyl-D-homopregna-1,4-diene-3,20-dione, there was obtained 21-acetoxy-17a-hydroxy-6α-methyl-D-homopregna-1,4-diene-3,11,20-trione; melting point 157°–159° C. (from acetone/hexane);

from 21-acetoxy-9-fluoro-11β,17a-dihydroxy-D-homopregna-1,4-diene-3,20-dione, there was obtained 21-acetoxy-9-fluoro-17a-hydroxy-D-homopregna-1,4-diene-3,11,20-trione; melting point 227° C.; $[\alpha]_D = +142°$ (c = 0.101% in dioxan); UV: $\epsilon_{235} = 15,300$;

from 9-fluoro-11β-hydroxy-17a,21-dipropionyloxy-D-homopregna-1,4-diene-3,20-dione, there was obtained 9-fluoro-17a,21-dipropionyloxy-D-homopregna-1,4-diene-3,11,20-trione; melting point 170°–171° C. (from acetone/hexane); UV: $\epsilon_{236} = 15,400$; $[\alpha]_D = +72°$ (c = 0.1% in methanol);

from 9-fluoro-11β,16a-dihydroxy-D-homopregna-1,4-diene-3,20-dione there was obtained 9-fluoro-17a-hydroxy-D-homopregna-1,4-diene-3,11,20-trione; melting point 252°–253° C.; UV: $\epsilon_{235} = 15,200$; $[\alpha]_D = +92°$ (c = 0.1% in dioxan); and from 17a,21-dibutyryloxy-9-fluoro-11β-hydroxy-D-homopregna-1,4-diene-3,20-dione there was obtained 17a,21-dibutyryloxy-9-fluoro-D-homopregna-1,4-diene-3,11,20-trione; melting point 129°–131° C.; UV: $\epsilon_{235} = 15,600$; $[\alpha]_D = +50°$ (c = 0.1% in dioxan).

The starting material used in the first paragraph of this Example was prepared as follows:

11β,17a,21-Trihydroxy-D-homopregna-1,4-diene-3,20-dione was reacted in pyridine with butyric acid anhydride to yield 21-butyryloxy-11β,17a-dihydroxy-D-homopregna-1,4-diene-3,20-dione; melting point 244°–246° C.; UV: $\epsilon_{243} = 14,380$; $[\alpha]_D = +111°$ (c = 0.1% in dioxan).

EXAMPLE 2

500 mg of 21-acetoxy-17a-hydroxy-D-homopregn-4-ene-3,11,20-trione and 350 mg of selenium dioxide were boiled at reflux for 40 hours under argon in 25 ml of tert.butanol and 0.25 ml of acetic acid. The mixture was filtered and the filtrate evaporated. The oil obtained was taken up in ethyl acetate and washed successively with sodium bicarbonate solution, water, ice-cold ammonium sulphide solution, dilute ammonia, water, dilute hydrochloric acid and water. The ethyl acetate solution was dried and evaporated in vacuo. Chromatography on silica gel gave 21-acetoxy-17a-hydroxy-D-homopregna-1,4-diene-3,11,20-trione; melting point 230°–231° C.; $[\alpha]_D = +162°$ (c = 0.103% in dioxan); UV: $\epsilon_{239} = 13,900$.

EXAMPLE 3

830 mg of 21-acetoxy-17a-hydroxy-D-homopregna-1,4-diene-3,11,20-trione in 25 ml of methanol were treated under argon with 550 mg of potassium carbonate in 5 ml of water and the mixture was stirred for 2 hours at room temperature. 0.5 ml of glacial acetic acid in 1.2 of methanol was then added and the mixture was poured on to water. The product was extracted with methylene chloride and the methylene chloride solutions were washed with sodium chloride solution, dried and evaporated. After filtration on silica gel with methylene chloride/acetone, 540 mg of 17a,21-dihydroxy-D-homopregna-1,4-diene-3,11,20-trione [melting point 222°–224° C.; $[\alpha]_D = +147°$ (c = 0.093% in dioxan); UV: $\epsilon_{239} = 13,700$] crystallised from acetone/hexane.

In an analogous manner, from 21-acetoxy-9-fluoro-17a-hydroxy-D-homopregna-1,4-diene-3,11,20-trione there was obtained 9-fluoro-17a,21-dihydroxy-D-homopregna-1,4-diene-3,11,20-trione; melting point 248°–249° C.; $[\alpha]_D = +137°$ (c = 0.103% in methanol); UV: $\epsilon_{235} = 15,450$.

EXAMPLE 4

(a) 500 mg of 17a,21-dihydroxy-9-fluoro-D-homopregna-1,4-diene-3,11,20-dione, 2.5 ml of tetrahydrofuran, 0.5 ml of triethyl orthopropionate and 25 mg of p-toluenesulphonic acid were stirred for 3.5 hours at room temperature. After the addition of 1 drop of pyridine, the mixture was diluted with methylene chloride, washed with sodium bicarbonate solution and water, dried and evaporated.

(b) The residue, 9-fluoro-3,11,20-trioxo-D-homopregna-1,4-dien-17a,21-ylenethyl orthovalerate, in 5 ml of methanol was treated with 1 ml of 2-N aqueous oxalic acid and the mixture was stirred for 20 minutes at room temperature. The mixture was diluted with methylene chloride, washed with water, sodium bicarbonate solution and dilute sodium chloride solution, dried and evaporated.

(c) The thus-obtained crude 9-fluoro-21-hydroxy-17a-propionyloxy-D-homopregna-1,4-diene-3,11,20-trione, 1 ml of propionic acid anhydride and 5 ml of pyridine were stirred for 4 hours at room temperature. After the addition of ice, the mixture was stirred for a further ca 30 minutes, then diluted with methylene chloride, washed with 2-N cold hydrochloric acid, dilute sodium bicarbonate solution and sodium chloride solution, dried over sodium sulphate and evaporated in vacuo. The residue, 9-fluoro-17a,21-dipropionyloxy-D-homopregna-1,4-diene-3,11,20-trione, was purified on silica gel and crystallised from acetone/hexane; melting point 170°–171° C.; UV: $\epsilon_{236} = 15,400$; $[\alpha]_D = +72°$ (c = 0.1% in methanol).

EXAMPLE 5

420 mg of 17a,21-dihydroxy-D-homopregna-1,4-diene-3,11,20-trione and 1.5 g of triphenylphosphine were stirred for 2 hours under argon at room temperature in 8 ml of dimethylformamide and 1.5 ml of carbon tetrachloride. The mixture was poured on to water and the product was extracted with methylene chloride. The methylene chloride solutions were washed, dried and evaporated in vacuo. Chromatography of the residue on silica gel gave 300 mg of 21-chloro-17a-hydroxy-D-homopregna-1,4-diene-3,11,20-trione; melting point 233°–234° C.; $[\alpha]_D = +175°$ (c = 0.103% in dioxan); UV: $\epsilon_{239} = 14,950$.

EXAMPLE 6

110 mg of 9-fluoro-17a,21-dihydroxy-D-homopregna-1,4-diene-3,11,20-trione in 10 ml of chloroform and 1 ml of propionic anhydride were treated with 50 mg of p-toluenesulphonic acid and the mixture was left to stand at room temperature for 1.5 hours. The chloroform solution was washed with sodium bicarbonate solution and water, dried and evaporated and the residue was dried under a high vacuum. 54 mg of 9-fluoro-17a-hydroxy-21-propionyloxy-D-homopregna-1,4-diene-3,11,20-trione crystallised from ether; melting point 204°–205° C.; $[\alpha]_D = +139°$ (c = 0.100% in dioxan); UV: $\epsilon_{235} = 15,350$.

EXAMPLE 7

A solution of 78 mg of chlorine in 1 ml of propionic acid was added to a solution of 0.416 g of 21-acetoxy-11β,17a-dihydroxy-D-homopregna-1,4-diene-3,20-dione in 10 ml of methylene chloride and 5 ml of ether at 0° C. and the mixture was left to stand for 18 hours at +4° C. For working-up, the mixture was poured on to ice-water and extracted with ether/methylene chloride. The extract was washed with cold, dilute sodium bicarbonate solution and then with water, dried over sodium sulphate and evaporated in vacuo at 30° C. The crude product was dissolved in 2 ml of pyridine and the solution was left to stand for 5 hours at room temperature. 40 ml of methylene chloride were then added to the solution and the mixture was washed with ice-cold 2-N hydrochloric acid, water, sodium bicarbonate solution until neutral. The methylene chloride solution was then dried over sodium sulphate and evaporated in vacuo. There was obtained 0.44 g of crude product which was chromatographed on 25 g of silica gel. Initially, a small amount of pure 21-acetoxy-2-chloro-11β,17a-dihydroxy-D-homopregna-1,4-diene-3,20-dione of melting point 241°–243° C. was eluted with ether/hexane. The subsequent fractions gave pure 21-acetoxy-2-chloro-17a-hydroxy-D-homopregna-1,4-diene-3,11,20-trione; melting point 228°–230° C.; UV: $\epsilon_{246} = 13,800$; $[\alpha]_D = +130°$ (c = 0.1% in dioxan).

EXAMPLE 8

0.5 g of 17a-hydroxy-21,21-diiodo-D-homopregna-1,4-diene-3,11,20-trione in 5 ml of acetone and 0.05 ml of acetone is treated with 0.5 g of dipotassium hydrogen phosphate and 0.03 ml of 85% orthophosphoric acid. The mixture is boiled at reflux under argon in the dark for 4 hours. 180 mg of sodium bicarbonate in 2.5 ml of water are then added and the acetone is removed by evaporation. After acidification with hydrochloric acid, there is obtained D-homoprednisone 21-phosphate as an amorphous precipitate; UV: $\epsilon_{239} = 13,000$.

The starting material can be prepared by oxidising 11β, 17a-dihydroxy-D-homopregna-1,4-diene-3,20-dione with chromic acid in acetone and reacting the resulting 17a-hydroxy-D-homopregna-1,4-diene-3,11,20-trione (UV: $\epsilon_{239} = 13,200$) in methanol with iodine in the presence of calcium chloride and calcium carbonate.

EXAMPLE 9

A solution of 1.5 g of 9-fluoro-17aα,21-dihydroxy-D-homopregna-1,4-diene-3,20-dione and 3.0 g of succinic acid anhydride in 30 ml of pyridine was kept at room temperature for 6 hours. For the working-up, the mixture was poured on to ice-water, acidified with dilute hydrochloric acid and extracted with methylene chloride. The organic extract was washed with water, dried over sodium sulphate and evaporated in vacuo. The residue was recrystallised from acetone/hexane. There was obtained pure 9-fluoro-D-homoprednisone 21-hemisuccinate; UV: $\epsilon_{235} = 15,100$.

We claim:

1. 9-Fluoro-17a-hydroxy-D-homopregna-1,4-diene-3,11,20-trione.

2. 21-Chloro-17a-hydroxy-D-homopregna-1,4-diene-3,11,20-trione.

* * * * *